US008933801B2

(12) United States Patent
Sweeney et al.

(10) Patent No.: US 8,933,801 B2
(45) Date of Patent: Jan. 13, 2015

(54) FALL DETECTION SYSTEM AND METHOD

(71) Applicant: Linear, LLC., Carlsbad, CA (US)

(72) Inventors: Jeffrey M. Sweeney, Carlsbad, CA (US); James J. Haflinger, Carlsbad, CA (US)

(73) Assignee: Linear LLC, Carlsbad, CA (US)

( * ) Notice: Subject to any disclaimer, the term of this patent is extended or adjusted under 35 U.S.C. 154(b) by 110 days.

(21) Appl. No.: 13/866,388

(22) Filed: Apr. 19, 2013

(65) Prior Publication Data

US 2014/0313036 A1 Oct. 23, 2014

(51) Int. Cl.

| | |
|---|---|
| *G08B 1/08* | (2006.01) |
| *G05B 23/02* | (2006.01) |
| *G08B 23/00* | (2006.01) |
| *G08B 5/22* | (2006.01) |
| *A61B 5/117* | (2006.01) |
| *G01C 19/00* | (2013.01) |
| *G01P 15/00* | (2006.01) |
| *G08B 21/04* | (2006.01) |

(52) U.S. Cl.

CPC .................................. *G08B 21/0446* (2013.01)
USPC .................. 340/539.11; 340/539.12; 340/3.1; 340/573.1; 340/6.1; 600/595; 702/104; 702/141; 73/488

(58) Field of Classification Search

CPC ............... G08B 21/02; G08B 21/0438; G08B 21/0446; G08B 21/04; G08B 21/043; G08B 21/0461; A61B 5/1117; G11B 5/54
USPC .............. 340/539.11, 539.12, 3.1, 573.1, 6.1; 702/104, 141; 600/595; 73/488
See application file for complete search history.

(56) References Cited

U.S. PATENT DOCUMENTS

| | | | | |
|---|---|---|---|---|
| 7,394,385 | B2 | 7/2008 | Franco et al. | 340/573.1 |
| 2006/0282021 | A1* | 12/2006 | DeVaul et al. | 600/595 |
| 2008/0129518 | A1* | 6/2008 | Carlton-Foss | 340/573.1 |
| 2010/0052896 | A1* | 3/2010 | Goodman | 340/539.11 |
| 2010/0176952 | A1* | 7/2010 | Bajcsy et al. | 340/573.1 |
| 2011/0025493 | A1 | 2/2011 | Papadopoulos et al. | 340/539.12 |
| 2011/0077865 | A1* | 3/2011 | Chen et al. | 702/3 |
| 2011/0218460 | A1* | 9/2011 | Masuzawa | 600/595 |
| 2012/0245735 | A1* | 9/2012 | Lee et al. | 700/255 |

* cited by examiner

*Primary Examiner* — George Bugg
*Assistant Examiner* — Munear Akki
(74) *Attorney, Agent, or Firm* — Schwegman Lundberg & Woessner, P.A.

(57) ABSTRACT

A fall detection method determines a fall detection algorithm based on sensor data aggregated from a plurality of fall detection devices. Sensor data is obtained from one of the plurality of fall detection devices not included in the aggregated sensor data. A probable fall event of the obtained sensor data is determined based on the fall detection algorithm. An alarm signal is generated based upon the determination of the probable fall event. A validity of the probable fall event is determined, and the fall detection algorithm is refined using the obtained sensor data and the validity of the probable fall event each time sensor data is obtained from any of the plurality of fall detection devices.

24 Claims, 6 Drawing Sheets

Sample Fall Event

FALL DETECTION SYSTEM AND METHOD

BACKGROUND OF THE INVENTION

1. Field of the Invention

This invention relates to a fall detection system and method thereof.

2. Description of Related Art

For many of the elderly and other individuals with physical limitations, the propensity to fall and the risk of injury therefrom increases over time. Serious injury due to a fall may prevent a person from immediately contacting a caregiver or medical personnel, thereby exacerbating any of the injuries suffered. Conventional solutions to this problem include providing a user with an apparatus worn on their person having a panic button that is pushed to alert others of a fall that requires help. However, the user may not always be able to push the button if their injury is severe.

Other solutions include a worn detection apparatus 600 (FIG. 6) having a fall detection sensor that incorporates an accelerometer and/or altimeter to record input data that is then processed using local firmware stored on apparatus 600 to determine the probability of a fall event. The apparatus contacts a predetermined authority such as server 610 and call center 620 upon determination that a fall event has likely occurred based on the sensor data. However, this functionality comes at the expense of increased size, manufacturing cost, and power consumption of the worn apparatus 600. In addition, any changes to how the fall event is determined by apparatus 600 requires a manual update, Requiring a user to update the firmware of apparatus 600 is time-consuming and may be impractical for the elderly and infirm.

U.S. Pat. No. 7,394,385 provides a monitoring system including a mobile unit having a panic button and an accelerometer. The accelerometer data is transmitted to a hub node and used to determine whether a client fell and to determine sleep patterns. An alarm may also be set when normal sleep patterns are not followed.

US 2011/0025493 discloses a wearable monitor including an accelerometer coupled to a user that detects a potential fall event. A user may adjust the values of configurable parameters used by the monitor to determine a potential fall event or a server may modify the parameters per user based on individual user data.

SUMMARY OF THE INVENTION

The present invention provides an adaptive fall detection system and method thereof having a continually refined fall detection algorithm providing the most accurate detection algorithm to a user at any given point in time based on data gathered from a plurality of users in the system. This evergreen fall detection algorithm is developed by aggregating data on an ongoing basis from a plurality of users for the benefit of each user. The algorithm applied by a first user is the best available algorithm at that moment in time resulting from an aggregate of fall event data from plural users of the system, and the algorithm is updated with each new set of input data. The invention also provides distributed intelligence and storage among system components.

A fall detection method according to one embodiment of the invention includes the steps of determining a fall detection algorithm based on sensor data aggregated from a plurality of fall detection devices. Sensor data is obtained from one of the plurality of fall detection devices not included in the aggregated sensor data. A probable fall event of the obtained sensor data is determined based on the fall detection algorithm. An alarm signal is generated based upon the determination of the probable fall event. A validity of the probable fall event is determined, and the fall detection algorithm is refined using the obtained sensor data and the validity of the probable fall event each time sensor data is obtained from any of the plurality of fall detection devices. The probable fall event determination is based on a most recently refined fall detection algorithm. The refined fall detection algorithm is based on an ever increasing sample size of sensor data in aggregate. The method is a progressive fall detection method that applies a plurality of versions of the fall detection algorithm to detect a fall. The validity of the probable fall event indicates that the obtained sensor data represents either a false-positive fall event, false-negative fall event, or confirms the fall event. The fall detection algorithm is further refined based on user characteristics and user fall history. The validity of the probable fall event is provided by a user of the fall detection device. The determination of the probable fall event is executed among a distributed intelligence. The refined fall detection algorithm is customized to each user. The sensor data includes accelerometer data including a drop phase, land phase and stay phase.

In another embodiment of the invention, a fall detection system comprises a plurality of fall detection devices each including a corresponding sensor. A relay device provides communication between the fall detection device and a server. The server determines a fall detection algorithm based on sensor data aggregated from the plurality of fall detection devices. One of the fall detection devices obtains sensor data not included in the aggregated sensor data, and the server includes a processor to determine a probable fall event of the obtained sensor data based on the fall detection algorithm, generate an alarm signal based upon the determination of the probable fall event, determine a validity of the probable fall event and refine the fall detection algorithm using the obtained sensor data and the validity of the probable fall event each time sensor data is obtained from any of the plurality of fall detection devices. The probable fall event is determined progressively in that a plurality of versions of the fall detection algorithm are applied to detect a fall. The server is provided in a cloud-based network. The server includes memory to store the aggregated sensor data and the refined fall detection algorithm. The refined fall detection algorithm is based on an ever increasing sample size of sensor data in aggregate. The fall detection device is further refined based on user characteristics and user fall history. A transmitter in the fall detection device transmits the validity of the probable fall event. The fall detection device may be worn loosely around the neck, attached to the wrist, fastened to a belt at the waist, or otherwise fastened to the user.

In yet another embodiment of the invention, a fall detection determining device comprises a receiver receiving sensor data aggregated from a plurality of fall detection devices and new sensor data from one of the plurality of fall detection devices not included in the aggregated sensor data. A processor determines a fall detection algorithm based on the sensor data aggregated from the plurality of fall detection devices, and the processor determines a probable fall event of the new sensor data based on the fall detection algorithm. A transmitter transmits an alarm signal based upon the determination of the probable fall event. The receiver receives a validity of the probable fall event, and the processor refines the fall detection algorithm using the new sensor data and the validity of the probable fall event each time sensor data is obtained from any of the plurality of fall detection devices. The fall detection determining device is a relay device providing communication between the fall detection device and a cloud-based network. The fall detection determining device is a server provided in a cloud-based network. The refined fall detection algorithm is based on an ever increasing sample size of sensor data in aggregate.

In yet another embodiment of the invention, a fall detection system includes a plurality of fall detection devices each including a corresponding sensor. Each of the fall detection devices obtains respective sensor data not included in the aggregated sensor data. A relay device provides communication between the fall detection device and a server. The fall detection devices, the relay device and the server each include a processor. Any combination of the fall detection device, the relay device and the server determines a fall detection algorithm based on sensor data aggregated from the plurality of fall detection devices, determines a probable fall event of the obtained sensor data based on the fall detection algorithm, generates an alarm signal based upon the determination of the probable fall event, determines a validity of the probable fall event and refines the fall detection algorithm using the obtained sensor data and the validity of the probable fall event each time sensor data is obtained from any of the plurality of fail detection devices. Any combination of the fail detection device, the relay device and the server provides storage into respective memory for the obtained sensor data, the aggregated sensor data, the fall detection algorithm, the probable fall event, the validity of the probable fall event, and the refined fall detection algorithm.

Other features and advantages of the invention will be apparent from the following detailed description, taken in conjunction with the accompanying drawings which illustrate, by way of example, various features of embodiments of the invention.

DETAILED DESCRIPTION OF THE INVENTION

Figure 1:
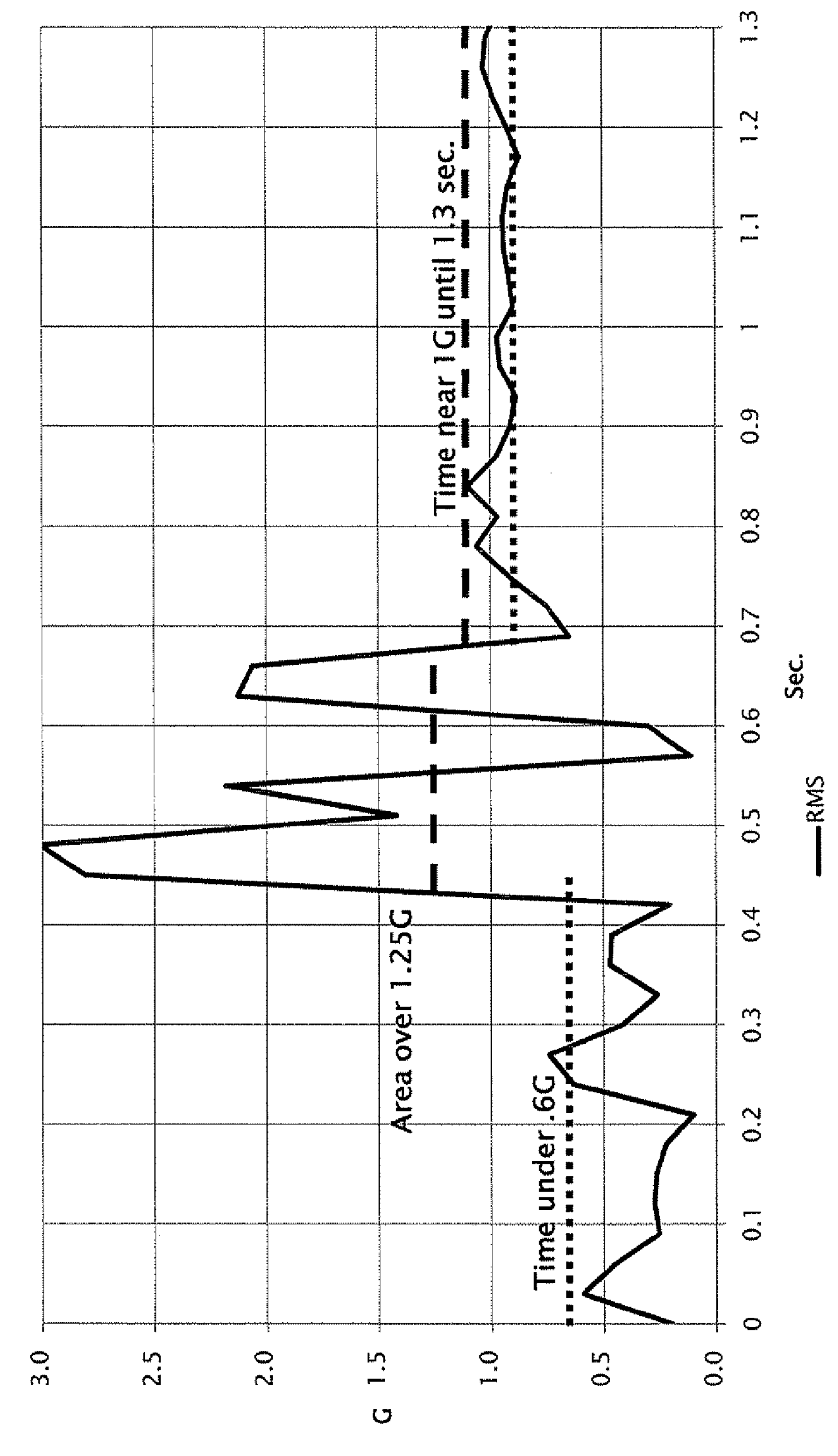
FIG. 1 illustrates accelerometer data of a fall event.

FIG. 1 is a graph of accelerometer data collected from a sensor coupled to a user for a two foot fall to a carpeted surface where g-forces are tracked over time. When there is no motion, the sensor only detects the force of gravity (1 g). Minor variations will occur due to routine motion, such as from walking, sitting down, picking up an object, etc.

As understood herein, a fall event is the rapid and generally uncontrolled, downward movement of an individual from a higher position to a lower position. The course of a fall event may be divided into three phases including a drop phase, a land phase and a stay phase. A fall begins with a drop phase that generally lasts about a half second and corresponds with a near 0 g event. For instance, free fall is a 0 g event and upon detection of free fall, sensor data will be collected for about 1.3 seconds. The drop phase in FIG. 1 lasts for about 0.4 seconds and fluctuates between 0 g and about 0.6 g. At the end of a fall when contact is made with a surface, the land phase generally produces at least a 1.2 g event for about another half second. For example, the land phase registers a reading of above 1.25 g for about 0.3 seconds in FIG. 1. Finally, in the stay phase, a near 1 g reading occurs without significant activity. In FIG. 1, the stay phase varies very near 1 g for at least 0.6 seconds. The exact values for each of these phases provides factors that describe an event as a fall event or some other type of non-fall movement.

Figure 2:
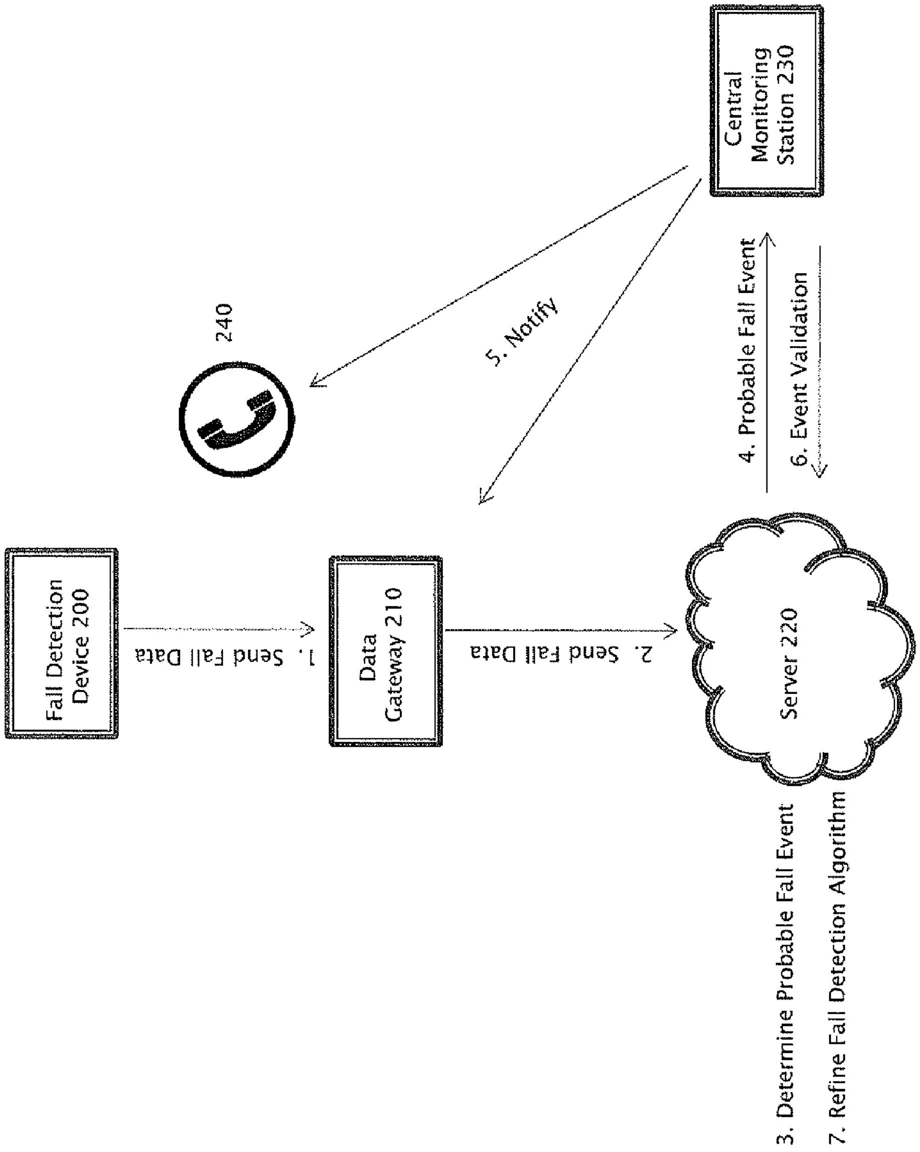
FIG. 2 is a block diagram of an embodiment of a fall detection system according to the present invention.

FIG. 2 illustrates a first embodiment of a fall detection system where the majority of the analytics, storage and decision processing is cloud based. The system includes fall detection device 200, data gateway 210 and server 220. Detection device 200 is worn by a user and includes at least a microprocessor, a transmitter and a sensor. The sensor may be a 3-axis accelerometer or the like to record data related to a fall event. Detection device 200 may be worn on the wrist like a watch, attached to the torso (i.e. clipped onto a belt), or worn around the neck like a pendant. Detection device 200 need not be firmly attached to the subject or to the subject's clothing. Detection device 200 may be a single purpose device, but is not limited to this form as the fall detection device may be incorporated with other sensors such as an altimeter, GPS or other types of devices such as a watch, cell phone, etc. Detection device 200 may also be worn or attached to the body or clothing of the user. Detection device 200 may include a switch or button for manually calling for help or to confirm a fall event. Furthermore, detection device 200 may alternatively include a transceiver for transmitting and receiving data from a data gateway.

Fall detection device 200 first detects a change in acceleration and collects sensor data. Device 200 performs an initial calculation to determine if the sensor data is a potential fall event that warrants further analysis based on low acceleration. When the sensor detects free fall (drop phase), then the sensor records additional data as potential fall event data for further analysis. This potential fall event data is sent at step 1 from fall detection device 200 to data gateway 210. Data gateway 210, or a relay device, provides connectivity between fall detection device 200 and external server 220, central monitoring station 230 and/or other external network/cloud service. In FIG. 2, the fall event data is sent at step 2 from data gateway 210 to server 220 located in the cloud where processing and storage of fall event data is provided in server 220.

Although the fall detection system of this invention will most often be managed by a central monitoring station, such as central monitoring station 230 described above, the system may be alternatively managed by another designated party such as a friend, family member, caregiver, etc. For example, in the event of fall detection or other emergency, the system may be configured to direct dial through a list of pre-designated phone numbers to reach the designated party. Thus, in the following description and claims, references to "central monitoring station" mean not only a central monitoring station in the traditional sense, but also any other designated party that receives and manages the fall detection or other emergency event.

A probable fall event is the algorithmic determination that sensor data represents a genuine fall event. The term probable denotes that the algorithm is subject to validation. However, the determination of a probable fall event is sufficient to proceed with an alarm signal and notification to a proper authority even if a user does not confirm that the event is a genuine fall. The determination of a probable fall event having occurred is based on an analysis of the transmitted potential fall event data of the user as input to the most recently updated fall detection algorithm. The algorithm incorporates aggregated fall event data from a plurality of users and corresponding validation data that either confirms the fall event as genuine or indicates a false-positive fall event that is not a genuine fall event. For example, the indication that the potential fall event data is not an actual fall event (false-positive) may be input by the user at fall detection device 200 and/or data gateway 210, or even by central monitoring station 230.

On the other hand, false-negative information and confirmation of non-fall events are also input and recorded by the system. A false-negative fall event corresponds to a fall event that is indicated by the user as genuine, but whose corresponding sensor data is determined by the fall detection algorithm to be a non-fall event. A confirmation of a non-fall event is the sensor data of an event that is closest to, but does not meet the threshold to be a probable fall event. The confirmation of a non-fall event may be transmitted from the fall detection device at a predetermined time interval, such as every hour. In this regard, it should be noted that if the user has operated the button or switch on fall detection device 200 to affirmatively request help, that any data collected regarding a near fall (false-negative fall event) just prior to the user pressing the button should be transmitted. In such case the user has likely fallen, even though the data collected did not pass the threshold for a fall.

Upon calculation and determination by a processor and/or controller circuitry that the received potential fall event data is a probable fall event based on the fall detection algorithm (step 3) or a false-negative is determined, an alarm signal is generated at server 220 and transmitted to central monitoring station 230 (step 4). The system may also be configured to route the alarm signal to data gateway 210 and/or another server (not shown). Central monitoring station 230 then notifies a designated responsible party 240 at step 5, which may include emergency personnel, caretakers, family and friends of the user, etc. Notification may be executed through voice communication or any known messaging protocol. Responsible party 240 may then communicate validation data to central monitoring station 230 to confirm whether the probable fall event is genuine or a false-positive. Depending on the result of the monitoring station's communication with the designated responsible party, central monitoring station 230 transmits a validation of the probable fall event as either genuine or a false-positive to server 220 at step 6. The validation may also be input and transmitted by data gateway 210. For example, a user can cancel the alarm signal at the data gateway by operation of a switch, button or voice communication through a microphone provided in the data gateway. Server 220 at step 7 then refines the fall detection algorithm to incorporate the fall event data transmitted at step 1 and corresponding fall event validation data transmitted at step 6. The false-negative information and confirmation of a non-fall event may also be used to refine the fall detection algorithm.

In addition, updates and refinements to the fall detection algorithm may be based on user characteristics such as age, health, lifestyle and so forth. User characteristic data may be transmitted by the detection device and data gateway, or stored in the server and linked to a detection device. The algorithm may also be refined based on the false-negative fall event and confirmation of non-fall event information. Thereafter, a subsequent potential fall event will be analyzed with an algorithm incorporating all the available data that is recorded and stored. Accordingly, a future potential fall event from any user of the system will immediately gain the improved accuracy of the up-to-date algorithm. Thus, the accuracy of the refined fall detection algorithm available to any user at a given moment in time is a result of data gathered from many other users in the system and made available to the single user in the form of the most updated refinement of the algorithm.

Although FIG. 2 illustrates the steps of determination of the probable fall event, transmission of an alarm signal and update of the algorithm performed at server 220, those steps may be performed as a whole or in part in fall detection device 200, data gateway 210 and server 220. Data gateway 210 may store and/or process events, data and algorithms in order to determine a probable fall event based on the potential fall event data transmitted from fall detection device 200. The algorithms used to determine the probable fall event may reside locally on data gateway 210, remotely in server 220, in the cloud or in some other external location. The alarm signal may also be generated from the cloud, server, data gateway or fall detection device. The fall detection device, data gateway and server include at least the necessary hardware as understood by those of ordinary skill in the art necessary to execute the operations described such as a microprocessor, controller circuitry, memory, as well as a receiver and/or transmitter necessary to perform wireless and/or wired communication.

Moreover, the fall detection device may also include a switch, button, a speaker for voice control or the like to allow the user to manually generate a validation signal indicating either a positive fall event or a false-positive fall event. The positive fall event generated by the user may be used to determine a false-negative fall event. The fall detection device also transmits confirmation of non-fall event data at predetermined intervals. Embodiments of the invention including such an aspect is described below with respect to FIGS. 3 and 4.

Figure 3:
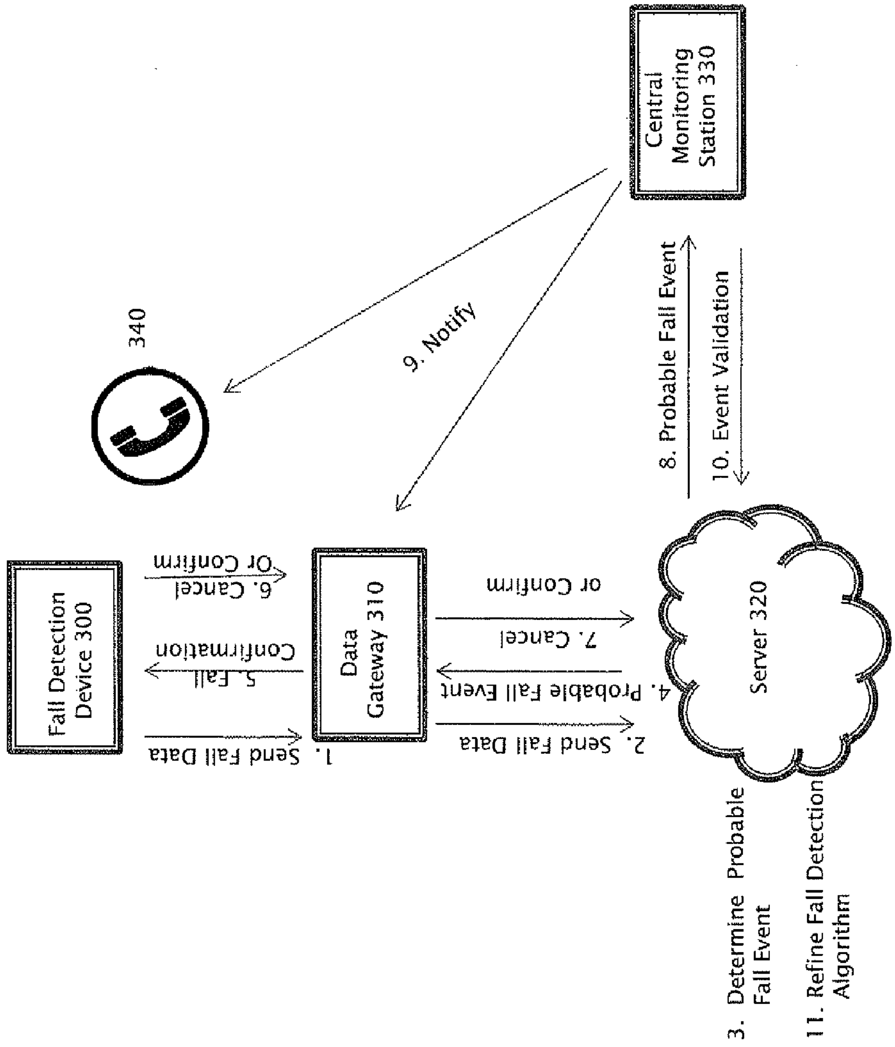
FIG. 3 is a block diagram of another embodiment of a fail detection system according to the present invention.

FIG. 3 illustrates a second embodiment of a fall detection system where the majority of the analytics and decision processing is cloud based. Fall detection device 300 begins by collecting sensor data. When the sensor detects free fall (drop phase), device 300 records additional data as potential fall event data for further analysis. This data includes confirmation of non-fall event data and sensor data recorded for a false-negative determination. This fall event data is sent at step 1 from device 300 to data gateway 310. The fall event data is sent at step 2 from data gateway 310 to server 320 located in the cloud. At step 3, the received fall event data is stored in memory and analyzed by controller circuitry using the most up-to-date, refined fall detection algorithm to determine if the received data represents a probable fall event. If the result of the calculation is that the received data is a probable fall event, then server 320 transmits an indication of a probable fall event to data gateway 310 at step 4. Data gateway 310 then transmits a fall validation request signal to device 300 at step 5, requesting that the user confirm the accuracy of the fall event determination at step 3. Furthermore, an algorithmic determination that the fall data does not represent a probable fall event may also prompt the server and gateway to request fall validation from a user at the fall detection device.

The user at step 6 transmits either a positive fall event or false-positive fall event validation signal from device 300 or data gateway 310. The user validation signal is then forwarded from data gateway 310 to server 320 at step 7. In this manner, device 300 allows the user to cancel or confirm a probable fall event as determined by the system. User cancellation will prohibit execution of steps 8-10. A lack of response from the user to the fall confirmation request signal after a predetermined amount of time may also serve as the basis to generate an alarm signal. A lack of response may indicate, for example, that the user is seriously injured from the fall and unable to operate device 300.

Next, an alarm signal is generated at server 320 and transmitted to central monitoring station 330 upon positive validation of the fall event or non-response (step 8). The system may also be configured to route the alarm signal of a probable fall event to data gateway 310 and/or another server (not shown). Central monitoring station 330 then notifies a responsible party 340 at step 9, which may include emergency personnel, caretakers, family and friends of the user, etc. Notification may be executed through voice communication or any known messaging protocol. Optionally, responsible party 340 may communicate validation data to central monitoring station 330 to confirm whether the probable fall event is genuine or a false-positive. Depending on the result of the monitoring station's communication with the designated responsible party, central monitoring station 330 also transmits a validation of the probable fall event as either genuine or a false-positive to server 320 at step 10.

Using the fall event data, corresponding validation data and user characteristic data, controller circuitry of server 320 at step 11 refines and updates the fall detection algorithm to improve the algorithm for subsequent potential fall events from any user. The false-negative fall event information and confirmation of a non-fall event transmitted and recorded by the system may also be input to refine the fall detection algorithm. As more positive fall events, false-positive fall events, false-negative fall events and confirmation of non-fall events are recorded and incorporated into the fall detection algorithm, the accuracy of the algorithm will improve. Each user of the system benefits from the aggregated data of all previous events as they are provided the most accurate fall detection algorithm possible at the time. Alternatively, server 320 may include cloud based data processing and storage, as well as signal routing.

Figure 4:
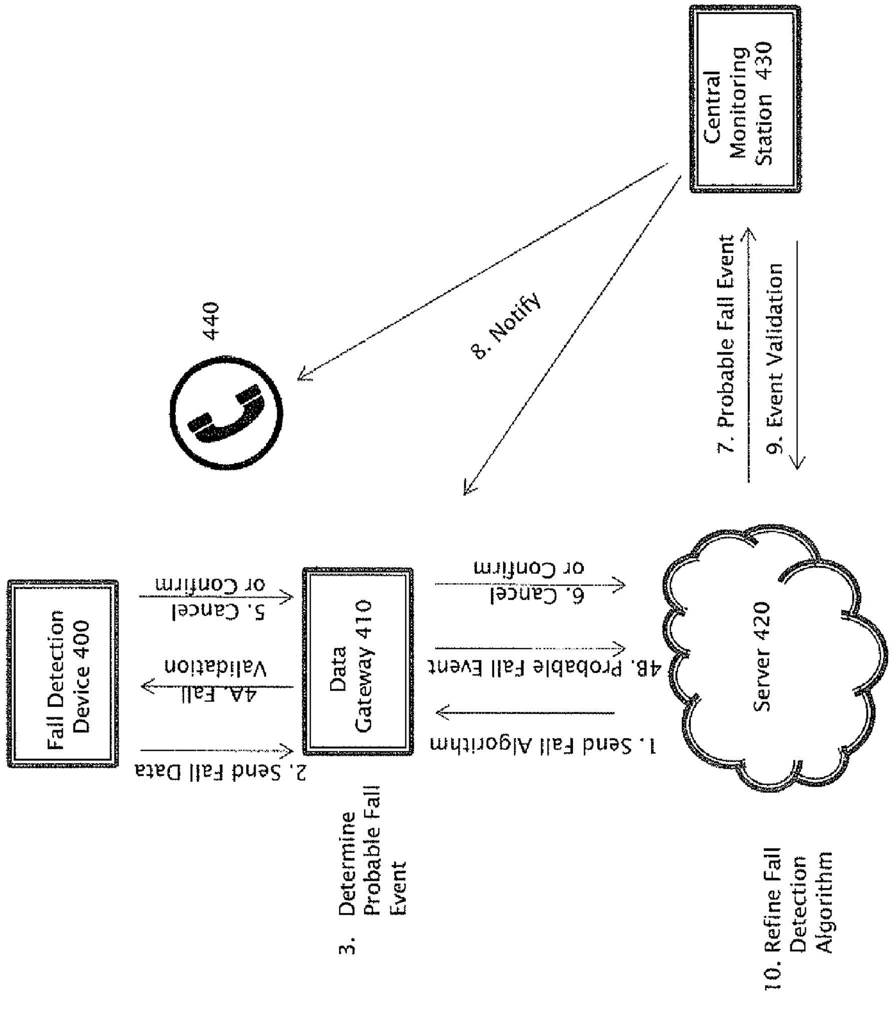
FIG. 4 is a block diagram of another embodiment of a fall detection system according to the present invention.

The operation in FIG. 4 is similar to that described in FIG. 3 except that the majority of the decision processing is performed in data gateway 410 instead of server 420. In particular, the determination of a probable fall event using the fall detection algorithm (step 3) is performed in data gateway 410 while the refining and updating of the fall detection algorithm (step 10) is performed in the cloud. Storage of the fall data and algorithm may be provided partially or wholly in the gateway and server.

At step 1, the most up-to-date fall detection algorithm is transmitted (pushed) from server 420 to data gateway 410. Thereafter, fall detection device 400 collects sensor data of a potential fall event. This fall event data is sent at step 2 from fall detection device 400 to data gateway 410. At step 3, the received fall event data is analyzed by controller .circuitry using the fall detection algorithm pushed to data gateway 410 at step 1 to determine if the received data represents a probable fall event. If the result of the calculation is that the received data is a probable fall event, then data gateway 410 transmits a fall validation request signal at step 4A to fall detection device 400. An indication of a probable fall event and the fall event data is also transmitted to server 420 and stored therein at step 4B.

Upon receiving the fall validation request signal, the user confirms the accuracy of the fall event determination performed at data gateway 410 and transmits either a positive or false-positive validation signal from detection device 400 to data gateway 410 (step 5). In this manner, device 400 allows the user to cancel or confirm a probable fall event as determined by the system. User cancelation will prohibit execution of steps 7-9. A lack of response from the user to the fall validation request signal after a predetermined amount of time may also serve as the basis to confirm the probable fall event and generate an alarm signal. The user validation signal is then forwarded from data gateway 410 to server 420 at step 6.

Assuming that the fall event is validated, an alarm signal is generated at server 420 and transmitted to central monitoring station 430 (step 7). The system may also be configured to route the alarm signal of a probable fall event to data gateway 410 and/or another server (not shown). Central monitoring station 430 then notifies a responsible party 440 at step 8, which may include emergency personnel, caretakers, family and friends of the user, etc. Notification may be executed through voice communication or any known messaging protocol. Optionally, responsible party 440 may communicate with central monitoring station 430 to validate whether the probable fall event is genuine or a false-positive. Depending on the result of the monitoring station's communication with the designated responsible party, central monitoring station 430 may transmit a validation of the probable fall event as either genuine or a false-positive to server 420 at step 9.

Based on either validation data received from device 400 or station 430, server 420 at step 10 refines the fall event algorithm using controller circuitry to incorporate the fall event data transmitted at step 4B and corresponding fall event validation data transmitted at steps 6, 9 to improve the algorithm for subsequent potential fall events from any user of the system. The false-negative information and confirmation of a non-fall event transmitted and recorded by the system may also be input to refine the fall detection algorithm. As more positive fall events, false-positive fall events, false-negative fall events and confirmation of non-fall events are recorded and incorporated into the fall detection algorithm, the accuracy of the algorithm will improve. In this manner, each user of the system benefits from the aggregated data of all previous events and users in order to provide the most accurate fall detection algorithm possible at the time.

Figure 5:
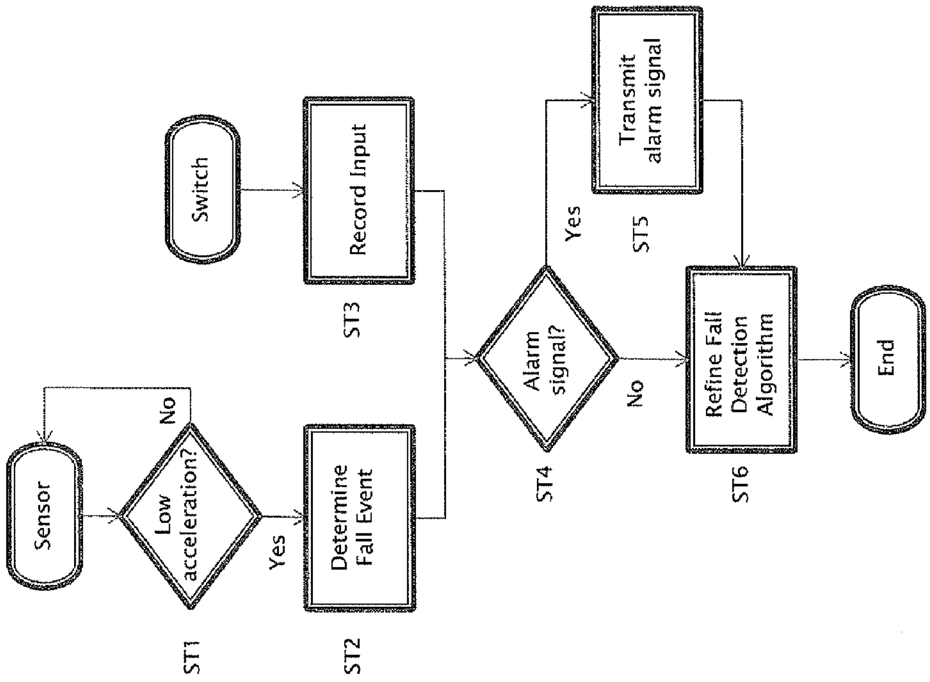
FIG. 5 is a flowchart of an embodiment of a fall detection process according to the present invention.
Figure 6:
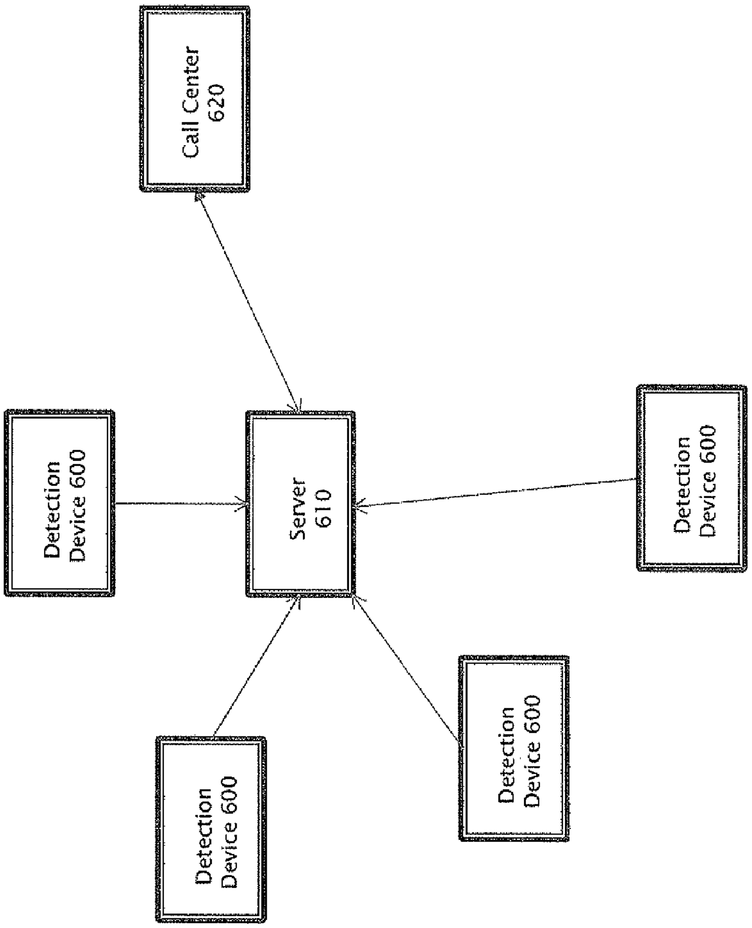
FIG. 6 PRIOR ART
FIG. 6 is a block diagram of a prior art fall detection system.

FIG. 5 is a flowchart of the fall detection process according to an embodiment of the invention. A sensor at step ST1 collects sensor data and determines whether or not the data represents low acceleration that may indicate a potential fall event. If the sensor data indicates low acceleration, more sensor data is collected and is input to a fall detection algorithm used to determine at step ST2 whether the sensor data represents a probable fall event. At step ST3, user input is recorded indicating a positive fall event, a false-positive fall event or no response. The results from steps ST2 and ST3 are then input to determine if an alarm signal should be generated at step ST4. For example, user input of a fall event will always result in generation and transmission of an alarm signal at step ST5, even if the determination at step ST2 determines a non-fall event (false-negative fall event). However, a determination at step ST2 of a probable fall event coupled with a user input of a false-positive results in the determination at step ST4 that no alarm signal be sent. Regardless of whether an alarm signal is transmitted or not, the data from steps ST2 and ST3 are used to further refine the fall detection algorithm at step ST6 and is provided to each user of the system. Furthermore, the algorithm may be customized based on user characteristics and user fall history. This refined detection algorithm is applied to the next set of sensor data collected so as to provide progressive, continual refinement and improvement of the algorithm and determination results. Thus, a plurality of versions of the fall detection algorithm are applied in the decision making process. Processing at this step may also include comparative analysis of older algorithms to the most updated algorithm.

Each of the embodiments described herein provides a fall detection system and method utilizing a fall event determination algorithm incorporating an ever increasing sample size of user data in aggregate. In this manner, the invention ensures that fall events are always analyzed using the most updated algorithm available and are also customizable to an individual user. A progressive decision making process is provided whereby the applied algorithm is progressively more recent, more refined and/or more rigorous so as to be more encompassing as the data from a probable fall event is transmitted and processed in a stage-gate manner from the fall detection device to the data gateway and from the data gateway to the server. The growing database of positive fall event data and false-positive fall event data, combined with user characteristics (i.e. age, health conditions, lifestyle, etc.) is a valuable resource in identifying risk factors and physical dynamics of fall events. Whether a genuine fall or a false-positive, the gateway and/or server stores the data for use in refining the algorithm. In addition, the growing accuracy of the system generates operational efficiencies by reducing the number of false-positive alarm events.

The size, cost and power consumption of the fall detection device is also minimized if the fall detection processing and storage is provided in the data gateway and/or server. The manufacturer and backend system provider of the fall detection system is also able to create a "service offering" in order to provide the updated fall detection algorithm.

The embodiments of the invention described in this document are illustrative and not restrictive. Modification may be made without departing from the spirit of the invention as defined by the following claims. For example, the data processing, analysis and data storage may be distributed throughout respective controller circuitry of the fall detection device, data gateway and server so as to share processing and decision making throughout the system. The data storage, algorithms and calculations performed may be performed by any combination of fall detection device, data gateway and the server. In other words, data storage and determination of a probable fall event may occur wholly or partially in the fall detection device, data gateway and server. Processing may also include comparative analysis of other fall detection algorithms. The fall detection device may be activated and deactivated remotely without having to send user additional hardware. Furthermore, different tiers of fall detection service may be offered. The data gateway may include a microphone and a speaker to allow the wearer of the fall detection device to communicate with an operator of the data gateway. The data gateway may also allow a user to cancel an outbound fall event alarm signal.

The invention claimed is:

1. A fall detection method comprising:

determining a fall detection algorithm based on sensor data aggregated from a plurality of fall detection devices;

obtaining sensor data from one of the plurality of fall detection devices not included in the aggregated sensor data;

determining a probable fall event of the obtained sensor data based on the fall detection algorithm;

generating an alarm signal based upon the determination of the probable fall event;

determining a validity of the probable fall event; and refining the fall detection algorithm using the obtained sensor data and the validity of the probable fall event each time sensor data is obtained from any of the plurality of fall detection devices.

2. The method of claim 1, wherein the probable fail event determination is based on a most recently refined fall detection algorithm.

3. The method of claim 1, wherein the refined fall detection algorithm is based on an ever increasing sample size of sensor data in aggregate.

4. The method of claim 1 is a progressive fall detection method that applies a plurality of versions of the fall detection algorithm to detect a fall.

5. The method of claim 1, wherein the validity of the probable fall event indicates that the obtained sensor data represents either a false-positive fall event, a false-negative fall event, or confirms the fall event.

6. The method of claim 1, wherein the fall detection algorithm is further refined based on user characteristics and user fall history.

7. The method of claim 1, wherein the validity of the probable fall event is provided by a user of the fall detection device.

8. The method of claim 1, wherein the determination of the probable fall event is executed among a distributed intelligence.

9. The method of claim 1, further comprising:

customizing the refined fall detection algorithm to each user.

10. The method of claim 1, wherein the sensor data includes accelerometer data including a drop phase, land phase and stay phase.

11. A fall detection system comprising:

a plurality of fall detection devices each including a corresponding sensor;

a relay device providing communication between the fall detection device and a server;

the server determining a fall detection algorithm based on sensor data aggregated from the plurality of fall detection devices, wherein one of the fall detection devices obtains sensor data not included in the aggregated sensor data; and the server includes a processor to determine a probable fall event of the obtained sensor data based on the fall detection algorithm, generate an alarm signal based upon the determination of the probable fall event, determine a validity of the probable fall event and refine the fall detection algorithm using the obtained sensor data and the validity of the probable fall event each time sensor data is obtained from any of the plurality of fall detection devices.

12. The fall detection system of claim 11, wherein the probable fall event is determined progressively in that a plurality of versions of the fall detection algorithm are applied to detect a fall.

13. The fall detection system of claim 11, wherein the server is provided in a cloud-based network.

14. The fall detection system of claim 11, wherein the server includes memory to store the aggregated sensor data and the refined fall detection algorithm.

15. The fall detection system of claim 11, wherein the refined fall detection algorithm is based on an ever increasing sample size of sensor data in aggregate.

16. The fall detection system of claim 11, wherein the fall detection device is further refined based on user characteristics and user fall history.

17. The fall detection system of claim 11, wherein a transmitter of the fall detection device transmits the validity of the probable fall event.

18. The fall detection system of claim 11, wherein the fall detection device is worn around a neck of a user.

19. A fall detection determining device comprising:

a receiver receiving sensor data aggregated from a plurality of fall detection devices and new sensor data from one of the plurality of fall detection devices not included in the aggregated sensor data;

a processor determining a fall detection algorithm based on the sensor data aggregated from the plurality of fall detection devices, and the processor determining a probable fall event of the new sensor data based on the fall detection algorithm;

a transmitter transmitting an alarm signal based upon the determination of the probable fall event, wherein the receiver receives a validity of the probable fall event, and the processor refines the fall detection algorithm using the new sensor data and the validity of the probable fall event each time sensor data is obtained from any of the plurality of fall detection devices.

20. The fall detection determining device of claim 19, wherein the fall detection determining device is a relay device providing communication between fall detection device and a cloud-based network.

21. The fall detection determining device of claim 19, wherein the fall detection determining device is a server provided in a cloud-based network.

22. The fall detection determining device of claim 19, wherein the refined fall detection algorithm is based on an ever increasing sample size of sensor data in aggregate.

23. A fall detection system comprising:

a plurality of fall detection devices each including a corresponding sensor, wherein each of the fall detection devices obtains respective sensor data not included in the aggregated sensor data;

a relay device providing communication between the fall detection device and a server; and the fall detection devices, the relay device and the server each including a processor, wherein any combination of the fall detection device, the relay device and the server determines a fall detection algorithm based on sensor data aggregated from the plurality of fall detection devices, determines a probable fall event of the obtained sensor data based on the fall detection algorithm, generates an alarm signal based upon the determination of the probable fall event, determines a validity of the probable fall event and refines the fall detection algorithm using the obtained sensor data and the validity of the probable fall event each time sensor data is obtained from any of the plurality of fall detection devices.

24. The fall detection system of claim 23, wherein any combination of the fall detection device, the relay device and the server provides storage into respective memory for the obtained sensor data, the aggregated sensor data, the fall detection algorithm, the probable fall event, the validity of the probable fall event, and the refined fall detection algorithm.

* * * * *

UNITED STATES PATENT AND TRADEMARK OFFICE

CERTIFICATE OF CORRECTION

PATENT NO. : 8,933,801 B2
APPLICATION NO. : 13/866388
DATED : January 13, 2015
INVENTOR(S) : Sweeney et al.

It is certified that error appears in the above-identified patent and that said Letters Patent is hereby corrected as shown below:

In the claims

In column 9, line 65, in Claim 2, delete “fail” and insert --fall--, therefor

Signed and Sealed this
Third Day of November, 2015

Michelle K. Lee
*Director of the United States Patent and Trademark Office*